United States Patent [19]

Smith, Jr. et al.

[11] Patent Number: 5,088,823
[45] Date of Patent: Feb. 18, 1992

[54] SPECTROANALYTICAL SYSTEMS

[75] Inventors: Stanley B. Smith, Jr., Punta Gorda, Fla.; Robert G. Schleicher, Winchester, Mass.

[73] Assignee: Thermo Jarrell Ash Corporation, Waltham, Mass.

[21] Appl. No.: 414,700

[22] Filed: Sep. 29, 1989

[51] Int. Cl.$^5$ .................. G01J 3/28; G01J 3/40; G01J 3/18
[52] U.S. Cl. .................. 356/328; 356/305; 356/334
[58] Field of Search ............. 356/305, 328, 334, 331

[56] References Cited

U.S. PATENT DOCUMENTS

| | | | |
|---|---|---|---|
| 3,658,423 | 4/1972 | Elliott | 356/328 |
| 4,494,872 | 1/1985 | Busch | 356/328 |
| 4,575,242 | 3/1986 | Akiyama et al. | 356/334 |
| 4,636,074 | 1/1987 | Levy et al. | 356/328 |
| 4,820,048 | 4/1989 | Barnard | 356/328 |
| 4,932,768 | 6/1990 | Gobeli | 350/611 |

OTHER PUBLICATIONS

McClintock, "A High Resolution Echelle Spectrograph Suitable for Astronomical Use at Both Far Ultraviolet and Visible Wave", Publications of Astrosociety, 10/79.
Boland et al., "An Echelle Spectrograph for High Resolution Studies of the Solar Vacuum Ultraviolet Spectrum", Solar Physics, 1971.
*An Echelle Spectrograph for High Resolution Studies of the Solar Vacuum Ultraviolet Spectrum*, Boland et al., Solar Physic, 1971.
*High Resolution Rocket EUV Solar Spectrograph*, Behring et al., Applied Optics, 3/73.
*A High Resolution Echelle Spectrograph Suitable for Astronomical Use at Both Far Ultraviolet and Visible Wave*, McClintock, Publications of Astro-Society, 10/79.

*Multielement Emission Spectrometry Using a CID Detector*, Sims, American Chemical Society, 1983.
Carbons et al., General Electric Company, Intelligent Vision Systems Operation, "Use of Charge Injectin Device Components in Still Cameras", 1983, Society of Photographic Scientists and Engineers.
M. B. Denton et al., "Charge-Injection and Charge-Coupled Devices in Practical Chemical Analysis", 1983 American Chemical Society.
G. R. Sims et al., "Multielement Emission Spectrometry Using a Charge-Injection Device Detector", 1983, American Chemical Society.
Jonathan V. Sweedler et al., "High-Performance", Analytical Chemistry vol. 60, No. 4, Feb. 14, 1988.
Patrick M. Epperson et al., "Application of Charge Transfer Devices in Spectroscopy", Analytical Chemistry, vol. 60, No. 5, Mar. 1, 1988.
R. B. Bilhorn et al., "Elemental Analysis with a Plasma Emission Echelle Spectrometer Employing a Charge Injection Device (CID) Detector", Applied Spectroscopy, vol. 1, 1989.

Primary Examiner—Davis L. Willis
Assistant Examiner—K. P. Hantis
Attorney, Agent, or Firm—Fish & Richardson

[57] ABSTRACT

A spectroanalytical system includes entrance aperture defining structure for receiving radiation to be analyzed along a first path; collimating structure in the first path for providing collimated radiation along a second path; fixed refraction structure in the second path for spatially separating (refracting) radiation in the second path in a first direction as a function of wavelength; fixed echelle grating structure in the second path for spatially separating the refracted radiation as a function of wavelength in a second direction orthogonal to the first direction and directing the orthogonally dispersed radiation in a beam along a third path that does not pass through the first refraction structure; and two-dimensional array detector structure for detecting the beam of orthogonally refracted radiation.

30 Claims, 2 Drawing Sheets

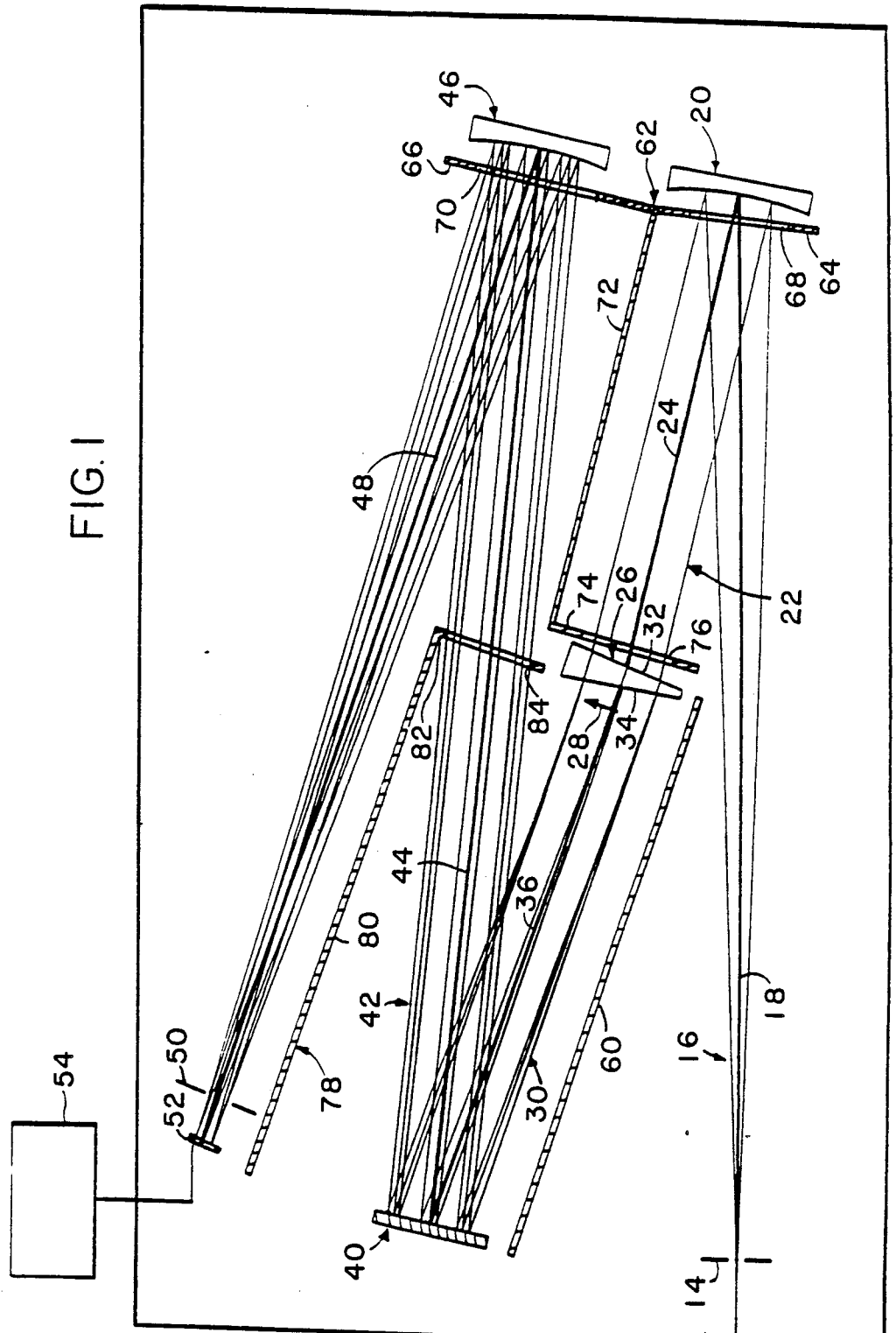
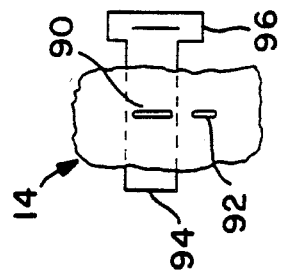
FIG. 1
FIG. 2

SPECTROANALYTICAL SYSTEMS

This invention relates to spectroscopy, and more particularly to spectroanalytical systems particularly adapted for analyzing complex samples.

Emission spectroscopy involves the obtaining of spectral information by exciting a sample to be analyzed to spectroemissive levels. Complex samples may contain twenty or more elements of interest over a range of concentrations. Each element emits radiation at different wavelengths in the vacuum UV to the near IR spectral region, and the intensities of spectral lines of analytical interest typically vary by several orders of magnitude.

A desirable spectroanalytical instrument simultaneously measures numerous emission lines and background as appropriate to quantitate each element of interest in a complex sample. In general, it is desirable to measure concurrently several emission lines in associated background regions for each element to reduce the chance of incorrect analyses caused by matrix interferences. Also, it is desirable to minimize the number of movable components of the spectroanalytical system as such minimization has a number of advantages, including increased reliability and enhanced reproducibility of analytical results.

In accordance with one aspect of the invention, there is provided a spectroanalytical system that includes entrance aperture defining structure for receiving radiation to be analyzed along a first path; collimating structure in the first path for providing collimated radiation along a second path; first refraction structure in the second path for spatially separating (refracting) radiation in the second path in a first direction as a function of wavelength; echelle grating structure in the second path for spatially separating the refracted radiation as a function of wavelength in a second direction orthogonal to the first direction and directing the orthogonally dispersed radiation in a beam along a third path that does not pass through the first refraction structure; and detector structure for detecting the beam of orthogonally refracted radiation.

Preferably, the detector structure is an addressable two-dimensional solid state multichannel detector array of the charge transfer type. Such detector arrays integrate signal information as light strikes them, much like photographic film. A typical individual detector in a charge transfer array of the CID (charge injection device) charge transfer type consists of several conductive electrodes overlying an insulating layer that forms a series of metal oxide semiconductor (MOS) capacitors. The insulator separates the electrodes from a photogenerated charge storage region. The amount of charge generated in a CID detector is measured either by moving the charge from the detector collector element to a charge sensing amplifier, or by moving the charge within the detector element and measuring the voltage change induced by this movement.

In plasma emission spectroscopy, a multichannel CID detector may perform nondestructive readouts of photogenerated charge packets so that integrated photogenerated charge from hundreds of spectral lines can be monitored while allowing a computer system to select an optimum integration period for each spectral line—intense lines being digitized early so that their intensity can be recorded before they saturate a detector element and weak spectral lines being recorded towards the end of a exposure so that the integration time is maximized. Further, the detector may simultaneously measure both emission lines and background, thus enhancing the ability to perform background corrections. Background and sample images may be subtracted from each other with precise spectral registration as the multichannel spectrometer has no moving parts.

In accordance with another aspect of the invention, there is provided a spectroanalytical system that includes entrance aperture defining structure for receiving radiation to be analyzed along a first path, the entrance aperture defining structure including structure for varying the effective height of the entrance aperture; collimating structure in the first path for collimating radiation in the first path and directing the collimated radiation along a second path; first refraction structure in the second path for spatially separating (refracting) the collimated radiation in the second path in a first direction as a function of wavelength; echelle grating structure in the second path for spatially separating the refracted radiation from the first refraction structure in a second direction orthogonal to the first direction as a function of wavelength; and detector structure for detecting the beam of orthogonally refracted radiation. This aspect provides increased wavelength range in a high resolution system.

Preferably, the entrance aperture structure includes first and second aligned slits of equal width disposed in the first path, one slit preferably having a height at least about twice the height of the other of the slits, and the structure for varying the effective height of the entrance aperture includes shutter structure for opening one slit or the other to pass radiation from the sample source to the collimating structure, the taller slit being adapted to be employed with shorter wavelength (e.g., UV) radiation, and the shorter slit being adapted to be employed with longer wavelength radiation and providing improved vertical resolution at longer wavelengths and lower orders. Preferably, the collimating structure, the first refraction structure, and the echelle grating structure are disposed in light tight housing structure; the first refraction structure is a prism of suitable material such as calcium fluoride, lithium fluoride or quartz; the echelle grating structure is of the reflective type; the angle between the first and second paths and the angle between the second and third paths are each less than twenty degrees; the system includes toric reflector structure in the third path for receiving the beam of orthogonally refracted radiation from the echelle grating structure and directing the orthogonally refracted radiation along a fourth path to the detector structure; baffle structure is disposed between the second and third paths for isolating radiation incident upon the echelle grating structure from radiation reflected from the echelle grating for reducing stray light interference; and similar baffle structure between the first and second paths, and between the third and fourth paths.

Also, preferably, the first refraction structure is disposed about halfway between the collimating structure and the echelle grating structure and provides dispersion over a five hundred nanometer wavelength range of about ten millimeters at the echelle grating, the blaze angle of the echelle grating is less than 25°, the echelle grating has less than two hundred grooves per millimeter, and the array detector has at least fifty thousand pixels. By appropriate selection and location of optical elements such as the prism, toric reflector and baffles, isolation between rays incident and reflected from the grating are enhanced, and optical aberrations, optical degradations and stray light are reduced.

In a particular embodiment, the housing structure has a width of less than forty centimeters, a length of less than eighty centimeters, and a height of less than thirty centimeters; and the system has a wavelength range of at least four hundred nanometers over at least twenty orders for analysis of a sample without movement of the collimating, first refraction, and echelle grating structures.

Other features and advantages will be seen as the following description of a particular embodiment progresses, in conjunction with the drawings, in which:

FIG. 1 is a diagrammatic view of a spectroanalytical system in accordance with the invention;

FIG. 2 is a diagrammatic view of entrance slit structure employed in the system shown in FIG. 1;

DESCRIPTION OF PARTICULAR EMBODIMENT

Figure 3:
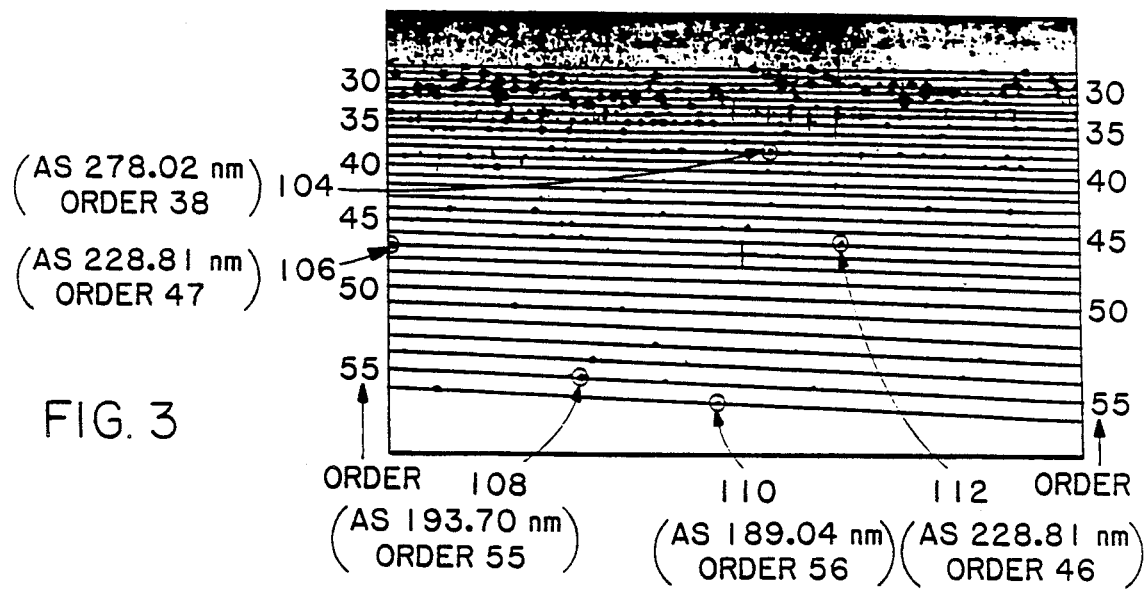
FIG. 3 is a echellogram of an arsenic sample analyzed with the spectroanalytical system of FIG. 1.

The spectroanalytical system shown in FIG. 1 is configured for atomic emission spectroscopy. The system includes an induction coupled plasma or other emission source 10 to which a complex sample is introduced for excitation to spectroemissive levels. The spectrometer includes housing 12 (about twenty-six centimeters wide, about fifty-three centimeters long and about fifteen centimeters high) with entrance structure slit 14 which allows radiation in the form of a beam 16, divergent about beam axis 18, to be incident upon a seventy-seven centimeter radius spherical collimating mirror 20, positioned about thirty-eight centimeters from entrance slit 14. Mirror 20 produces a substantially collimated beam 22 along beam axis 24 which is at an angle of about thirteen degrees to beam axis 18 and incident on calcium fluoride prism 26 that has planar faces that diverge at 11.5° and is positioned about seventeen centimeters from mirror 20.

Prism 26 disperses the incident radiation as a function of a wavelength in the direction of arrow 28 in beam 30; the degree of dispersion being a function of wavelength where shorter wavelengths are dispersed to a greater degree, as known. In the embodiment of FIG. 1, the receiving surface 32 of prism 26 is at approximately 87 degrees with respect to the axis 24 of the incident collimated beam; and opposing surface 34 is at an angle of 11.5 degrees with respect to surface 32. Central ray 36 is refracted by prism 26 at approximately 18.7 degrees to incident beam ray 24 and the prism provides dispersion over a 160–800 nanometer wavelength range of about ten millimeters at the echelle grating 40. The echelle grating 40 has sixty-three grooves per millimeter and a blaze angle of 19.5 degrees, is positioned about twenty centimeters from prism 26 and is fixed in position at a 19.5° angle (in the plane of FIG. 1) with respect to beam axis 36 and at a 6.5° angle perpendicular to the plane of FIG. 1. The radiation is dispersed by grating 40 in beam 42 in a direction perpendicular (orthogonal) to the refraction of the prism 26, i.e., out of the plane of FIG. 1. The orthogonally dispersed radiation thus is spatially separated in a two dimensional array as a function of wavelength and order. Central ray 44 is reflected from grating at about 5.3 degrees and the orthogonally dispersed radiation is received by toric mirror 46 (Y axis about 75 centimeters radius; X axis about 77 centimeters radius) which directs radiation along axis 48 through exit slit 50 and upon CID array detector 52 (CIDTEC 17) that has about ninety-five thousand pixels in a 6.6×8.8 millimeter photoactive area. Detector 52 is connected to output circuitry 54 for readout, signal processing and display of the resulting echellogram.

A system of opaque baffle members limit stray light and cross-talk between light beams formed by the optical elements. A first sheet metal baffle 60 (about twenty-five centimeters long and about fifteen centimeters high) separates the incident beam along axis 18, from prism 26 and grating 40. Sheet metal baffle 62 has a pair of rectangular plate sections 64, 66 (each about eight centimeters long), oriented to one another at an angle of 6°, with a rectangular aperture 68,70 (about four centimeters by five centimeters) in each section. Section 64 is positioned for isolating collimating mirror 24 and section 66 isolates toric mirror 46. Isolation baffle 72 extends between baffle 62 and prism 26 and serves to isolate the collimated beam (axis 24) from the beam (axis 44) reflected from grating 40. Prism baffle 74 has a rectangular open area 76 (about four centimeters on a side). Output baffle 78 has a first portion 80 (about fifteen centimeters long) and a right angle second portion 82 (about five centimeters long) with a rectangular open area 84 (about four centimeters on a side). Baffle 78 isolates the beam reflected from toric mirror 46 (axis 48) from the beam reflected from grating 40 (axis 44). Each baffle 60, 64, 72, 74, 80 and 82 extends between the top and bottom walls of housing 12 and has a height of about fifteen centimeters.

As illustrated in FIG. 2, the entrance slit structure 14 includes upper slit 90 that has a width of twenty-five micrometers and a height of one hundred fifty micrometers and aligned lower slit 92 that has a width of twenty-five micrometers and a height of seventy-five micrometers, and shutter mechanism 94 that is movable by an operating mechanism (diagrammatically indicated at 96) between a lower position that selects slit 90 and an upper position that selects lower slit 92. Slit 90 is employed with shorter wavelength (e.g., UV) radiation, and slit 92 is employed with longer wavelength radiation and provides improved vertical resolution at longer wavelengths and lower orders.

In operation, the shutter mechanism opens the desired slit 90 or 92, the sample to be analyzed is energized by the induction coupled plasma source 10 to spectroemissive levels, the resultant radiation that passes through entrance slit 14 is orthogonally dispersed by prism 26 and grating 40, and that orthogonally dispersed radiation is sensed by detector 52 and stored as photogenerated charge for reading by output circuitry 54 to produce an echellogram.

Shown in FIG. 3 is an echellogram of the output of detector 52 produced from excitation of an arsenic sample. The illustrated detection area covers a wavelength range from about 495 nanometers to about 511 nanometers at the upper (order 28) row 100 of pixels to 173 nanometers to 179 nanometers at the lower (order 56) row 102 of pixels. Characteristic detected emission lines 104–112 for the arsenic sample are indicated in FIG. 3 (the wavelength and order number being given in parentheses). For example, the phosphor spot 112 is produced by the 46th order of the 228.81 nanometer wavelength emission line. The spectroanalytical system provides multiple high resolution spectral readouts indicative of plural elements in the sample being analyzed.

Figure 4A:
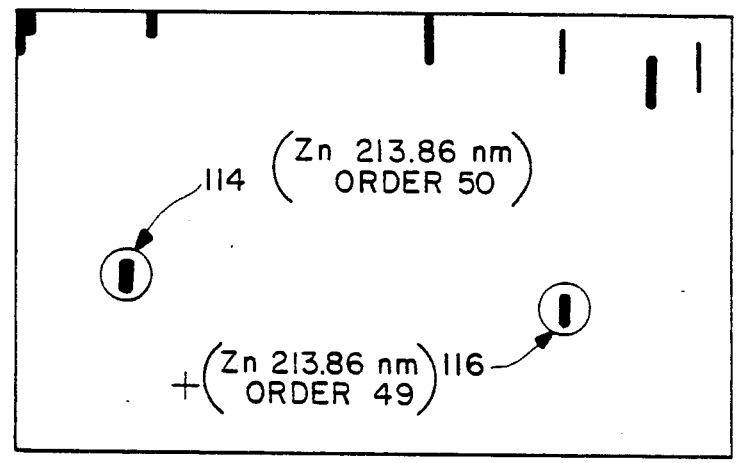
FIGS. 4a and 4b are echellograms that compare the resolution of a zinc sample in the spectroanalytical system of FIG. 1 with and without a toric mirror.
Figure 4B:
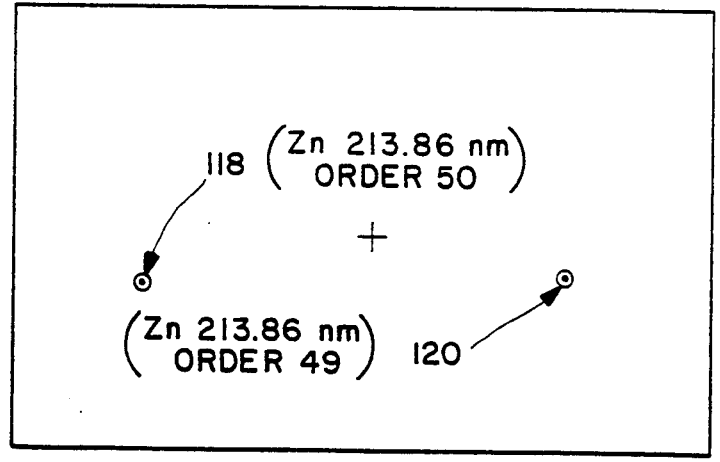

FIGS. 4a and 4b demonstrate the improvement provided by the use of toric mirror 46 in measuring spectral output of a zinc discharge lamp. In FIG. 4a, the 213.86 nanometer emission images 114, 116 from the CID detector 52 are shown for spectrometer configured with a spherical mirror in place of toric mirror 46. In FIG. 4b, the output is shown for a similar spectrometer including toric mirror 46 as in FIG. 1. The resolution enhancement using the toric mirror is evident, for example, the 213.86 nanometer emission images 118, 120 in FIG. 4b fall on areas about one-fifth the size of image areas 114, 116 in FIG. 4a.

While a particular embodiment of the invention has been shown and described, various modifications will be apparent to those skilled in the art, and therefore it is not intended that the invention be limited to the disclosed embodiment, of to details thereof, and departures may be made therefrom within the spirit and scope of the invention.

What is claimed is:

1. A spectroanalytical system comprising:
   entrance aperture defining structure for receiving radiation to be analyzed along a first path;
   collimating structure in said first path for collimating radiation in said first path and directing said collimated radiation along a second path;
   first refraction structure in said second path of said radiation for spatially separating (refracting) said collimated radiation in said second path as a function of wavelength in a first direction generally parallel to a plane defined by said first and second paths;
   echelle grating structure in said second path for spatially separating said refracted radiation from said first refraction structure in a second direction orthogonal to said first direction and directing said orthogonally refracted radiation in a beam along a third path that does not pass through said first refraction structure, wherein, an angle is formed between the first and second paths and an angle is formed between the second and third paths; and
   detector structure for detecting said beam of orthogonally refracted radiation.

2. The spectroanalytical system of claim 1 wherein said first refraction structure includes a prism.

3. The spectroanalytical system of claim 2 wherein the material of said prism is selected from the group consisting of quartz, calcium fluoride and lithium fluoride.

4. The spectroanalytical system of claim 2 wherein said prism is disposed in said second path about halfway between said collimating structure and said echelle grating structure.

5. The spectroanalytical system of claim 1 wherein the angle between said first and second paths and the angle between said second and third paths are each less than twenty degrees.

6. The spectroanalytical system of claim 1 and further including light tight housing structure in which said collimating structure, said first refraction structure, and said echelle grating structure are disposed.

7. The spectroanalytical system of claim 6 wherein said housing structure has a width of less than forty centimeters, a length of less than eighty centimeters, and a height of less than thirty centimeters; and said system has a wavelength range of at least four hundred nanometers over at least twenty orders for analysis of a sample without movement of said collimating structure, said first refraction structure, and said echelle grating structure.

8. The spectroanalytical system of claim 1 further including toric reflector structure in said third path for receiving said beam of orthogonally refracted radiation from said echelle grating structure and directing said orthogonally refracted radiation along a fourth path to said detector structure.

9. The spectroanalytical system of claim 8 and further including baffle structure between said third and fourth paths.

10. The spectroanalytical system of claim 1 wherein said echelle grating structure is reflective, and further including baffle structure disposed between said second and third paths for isolating radiation incident upon said echelle grating structure from radiation reflected from said echelle grating structure for reducing stray light interference.

11. The spectroanalytical system of claim 1 wherein said collimating structure includes a spherical mirror positioned in said first path to collect said radiation from said entrance aperture and direct a collimated beam of radiation along said second path to said first refraction structure.

12. The spectroanalytical system of claim 11 and further including baffle structure extending between said first and second paths.

13. The spectroanalytical system of claim 1 wherein said detector structure includes a solid state, two-dimensional multichannel detector array.

14. The spectroanalytical system of claim 13 wherein said array detector is a charge transfer array and has at least fifty thousand pixels per square centimeter of detection area.

15. The spectroanalytical system of claim 1 wherein said echelle grating structure has less than two hundred grooves per millimeter, the blaze angle of said echelle grating is less than 25°, and said first refraction structure means is a prism that provides dispersion over a five hundred nanometer wavelength range of at least about ten millimeters at said echelle grating structure.

16. The spectroanalytical system of claim 15 wherein said prism is disposed in said second path about halfway between said collimating structure and said echelle grating structure.

17. The spectroanalytical system of claim 1 and further including light tight housing structure in which said collimating structure, said first refraction structure, and said echelle grating structure are disposed, said housing structure having a width of less than forty centimeters, a length of less than eighty centimeters, and a height of less than thirty centimeters; said first refraction structure is a prism that provides dispersion over a five hundred nanometer wavelength range of at least about ten millimeters at said echelle grating structure; and said system has a wavelength range of at least four hundred nanometers over at least twenty orders for analysis of a sample without movement of said collimating structure, said first refraction structure, and said echelle grating structure.

18. The spectroanalytical system of claim 17 wherein the material of said prism is selected from the group consisting of quartz, calcium fluoride and lithium fluoride.

19. The spectroanalytical system of claim 17 wherein the angle between said first and second paths and the angle between said second and third paths are each less than twenty degrees.

20. The spectroanalytical system of claim 17 further including toric reflector structure in said third path for receiving said beam of orthogonally refracted radiation from said echelle grating structure and directing said orthogonally refracted radiation along a fourth path to said detector structure.

21. The spectroanalytical system of claim 17 wherein said detector structure includes a solid addressable two-dimensional multichannel charge injection device detector array and has at least fifty thousand pixels per square centimeter of detection area.

22. The spectroanalytical system of claim 17 wherein said echelle grating structure is reflective and further including baffle structure disposed between said second and third paths for isolating radiation incident upon said echelle grating structure from radiation reflected from said echelle grating structure for reducing stray light interference.

23. The spectroanalytical system of claim 22 wherein said collimating structure includes a spherical mirror positioned in said first path to collect said radiation from said entrance aperture and direct a collimated beam of radiation along said second path to said first refraction structure; and further including first baffle structure extending between said first and second paths; second baffle structure extending between said second and third paths; toric reflector structure in said third path for receiving said beam of orthogonally refracted radiation from said echelle grating structure and directing said orthogonally refracted radiation along a fourth path to said detector structure; and third baffle structure between said third and fourth paths.

24. The spectroanalytical system of claim 23 wherein said prism is disposed in said second path about halfway between said collimating structure and said echelle grating structure, and said detector structure is a solid state, addressable two-dimensional multichannel charge injection device detector array that has at least fifty thousand pixels per square centimeter of detection area.

25. A spectroanalytical system comprising:
entrance aperture defining structure for receiving radiation to be analyzed along a first path, said entrance aperture defining structure including a plurality of aligned slits disposed in said first path, one of said slits having a height at least about twice the height of another of said slits;
collimating structure in said first path for collimating radiation in said first path and directing said collimated radiation along a second path;
shutter structure for selectively opening said slits to pass radiation from a sample source along said first path to said collimating structure;
first refraction structure in said second path of said radiation for spatially separating said collimated radiation in said second path as a function of wavelength in a first direction;
echelle grating structure in said second path for spatially separating said refracted radiation from said first refraction structure in a second direction orthogonal to said first direction and directing said orthogonally refracted radiation in a beam along a third path that does not pass through said first refraction structure; and
detector structure for detecting said beam of orthogonally refracted radiation.

26. A spectroanalytical system comprising:
entrance aperture defining structure for receiving radiation to be analyzed along a first path; said entrance aperture defining structure including first and second aligned slits of equal width disposed in said first path, one of said slits having a height at least about twice the height of the other of said slits;
collimating structure in said first path for collimating radiation in said first path and directing said collimated radiation along a second path;
structure for varying the effective height of the entrance aperture including shutter structure for opening one slit or the other to pass radiation to said collimating structure, the taller of said slits being employed with shorter wavelength radiation, and the shorter of said slits being employed with longer wavelength radiation;
first refraction structure in said second path for spatially separating said collimated radiation in said second path in a first direction as a function of wavelength;
echelle grating structure in said second path for spatially separating said refracted radiation from said first refraction structure in a second direction orthogonal to said first direction as a function of wavelength; and
detector structure for detecting said beam of orthogonally refracted radiation.

27. The spectroanalytical system of claim 26 wherein said echelle grating structure directs said orthogonally refracted radiation in a beam along a third path that does not pass through said first refraction structure; and said first refraction structure is disposed in said second path about halfway between said collimating structure and said echelle grating structure.

28. The spectroanalytical system of claim 26 wherein said detector structure includes a solid addressable two-dimensional multichannel charge transfer detector array and has at least fifty thousand pixels per square centimeter of detection area.

29. The spectroanalytical system of claim 27, wherein said collimating structure includes a mirror positioned in said first path to collect said radiation from said entrance aperture and direct a collimated beam of radiation along said second path to said first refraction structure; and further including first baffle structure extending between said first and second paths; second baffle structure extending between said second and third paths; toric reflector structure in said third path for receiving said beam of orthogonally refracted radiation from said echelle grating structure and directing said orthogonally refracted radiation along a fourth path to said detector structure; and third baffle structure between said third and fourth paths.

30. A spectroanalytical system comprising:
entrance aperture defining structure for receiving radiation to be analyzed along a first path;
said entrance aperture defining structure including a plurality of aligned slits disposed in said first path, said slits having graduated heights,
collimating structure including a spherical mirror in said first path for collimating radiation in said first path and directing said collimated radiation along a second path;
shutter structure for selectively opening said slits to pass radiation from a sample source to said collimating structure, a taller one of said slits being employed with shorter wavelength radiation, and a shorter one of said slits being employed with longer wavelength radiation, prism structure disposed in said second path for spatially separating said collimated radiation in said second path as a function of wavelength in a first direction;

reflective echelle grating structure in said second path for spatially separating said refracted radiation from said prism structure in a second direction orthogonal to said first direction and directing said orthogonally refracted radiation in a beam along a third path that does not pass through said prism structure;

said prism structure being disposed in said second path about halfway between said collimating structure and said echelle grating structure and providing dispersion over a five hundred nanometer wavelength range of at least about ten millimeters at said echelle grating structure;

a solid state, addressable two-dimensional multichannel charge injection device detector array that has at least fifty thousand pixels per square centimeter of detection area for detecting said beam of orthogonally refracted radiation;

first baffle structure extending between said first and second paths; second baffle extending between said second and third paths;

toric reflector structure in said third path for receiving said beam of orthogonally refracted radiation form said echelle grating structure and directing said orthogonally refracted radiation along a fourth path to said detector array;

third baffle structure between said third and fourth paths; and light tight housing structure in which said collimating structure, said prism structure, and said echelle grating structure are disposed, said housing structure having a width of less than forty centimeters, a length of less than eighty centimeters, and a height of less than thirty centimeters;

said system having a wavelength range of at least four hundred nanometers over at least twenty orders for analysis of a sample without movement of said collimating structure, said prism structure, and said echelle grating structure.

* * * * *

UNITED STATES PATENT AND TRADEMARK OFFICE
CERTIFICATE OF CORRECTION

PATENT NO. : 5,088,823

DATED : February 18, 1992

INVENTOR(S) : Stanley B. Smith, Jr. et al.

It is certified that error appears in the above-identified patent and that said Letters Patent is hereby corrected as shown below:

On the title page, item [56]:
In the References Cited section:
    Reference No. 3, line 3, "physic" should be --physics--.
    Reference No. 7, line 1, "Carbons" should be --Carbone--.
    Reference No. 11, line 1, "Application" should be
            --applications--.

Col. 7, claim 21, line 10, after "solid" insert --state--.

Col. 8, claim 28, line 37, after "solid" insert --state--.

Col. 8, claim 29, line 42, after "a" insert --spherical--.

Signed and Sealed this

Fourth Day of May, 1993

Attest:

Attesting Officer

MICHAEL K. KIRK

Acting Commissioner of Patents and Trademarks